United States Patent
Janka et al.

(10) Patent No.: US 9,604,896 B2
(45) Date of Patent: Mar. 28, 2017

(54) HALOGEN-FREE CATALYST SYSTEM AND METHOD FOR PRODUCING BENZOIC ACID

(71) Applicant: Eastman Chemical Company, Kingsport, TN (US)

(72) Inventors: Mesfin Ejerssa Janka, Kingsport, TN (US); Charles Edwan Sumner, Jr., Kingsport, TN (US); Stephanie Nicole Rollins-Testerman, Kingsport, TN (US); Craig Steven Dunn, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/475,677

(22) Filed: Sep. 3, 2014

(65) Prior Publication Data

US 2014/0371484 A1    Dec. 18, 2014

(51) Int. Cl.
  *C07C 51/265*  (2006.01)
  *B01J 31/04*  (2006.01)
  *B01J 31/26*  (2006.01)

(52) U.S. Cl.
  CPC ............ *C07C 51/265* (2013.01); *B01J 31/04* (2013.01); *B01J 31/26* (2013.01); *B01J 2231/70* (2013.01)

(58) Field of Classification Search
  None
  See application file for complete search history.

(56) References Cited

U.S. PATENT DOCUMENTS

| 2,673,217 | A | | 3/1954 | Hull | |
| 2,963,509 | A | * | 12/1960 | Barker | C07C 51/265 562/416 |
| 4,339,599 | A | | 7/1982 | Jongsma | |
| 6,670,502 | B1 | * | 12/2003 | Codignola | C07C 51/265 562/409 |

FOREIGN PATENT DOCUMENTS

| CN | 102219662 A | 10/2011 |
| JP | 59-134734 | 8/1984 |
| JP | 10-182548 | 7/1998 |

OTHER PUBLICATIONS

Chester, Arthur W., et al.; "Zirconium Cocatalysis of the Cobalt-Catalyzed Autoxidation of Alkylaromatic Hydrocarbons"; Journal of Catalysis, vol. 46; 1977; pp. 308-319.

Partenheimer, W.; "Methodology and scope of metal/bromide autoxidation of hydrocarbons"; Catalysis Today, vol. 23; 1995; pp. 69-158.

Sheldon, Roger A. and Kochi, Jay K.; "Chapter 10 Aromatic Hydrocarbons"; Metal-Catalyzed Oxidations of Organic Compounds; 1981; pp. 315-339.

* cited by examiner

*Primary Examiner* — Sudhakar Katakam
*Assistant Examiner* — Ana Z Muresan

(57) ABSTRACT

Disclosed is a halide-free catalyst system and method for oxidizing toluene to form benzoic acid in benzoic acid solvent. The catalyst system contains Co, at least one of Zr and Hf, and an alkali metal basic salt.

13 Claims, No Drawings

HALOGEN-FREE CATALYST SYSTEM AND METHOD FOR PRODUCING BENZOIC ACID

FIELD OF THE INVENTION

The invention generally relates to a catalyst system and method for producing benzoic acid from toluene.

BACKGROUND OF THE INVENTION

A common method for making benzoic acid is by catalytically oxidizing toluene. The oxidation is typically carried out in benzoic acid solvent and is catalyzed by a Co/Mn/Br catalyst system where the bromide acts as a catalyst promoter. Acetic acid can be used as solvent, but benzoic acid is preferred in order to simplify purifying the product. The oxidation is generally performed in a continuous process where toluene is fed to a reaction zone, and the product is removed at the same rate and purified by distillation.

The corrosive nature of the bromide promoter, however, restricts the materials of construction of the oxidation reactor to more expensive materials, such as titanium or nickel alloys. Less expensive materials, such as 304-stainless steel, have been avoided because bromide salts can readily corrode them. Thus, a catalyst system that does not employ bromide is of great value in that it would allow the construction of a manufacturing plant at a much lower cost, and would even allow the use of general, multi-purpose equipment.

It is well known that toluene can be smoothly oxidized to benzoic acid in acetic acid solution using an oxidation catalyst composed of only cobalt salts without the need for a bromide promoter. The co-oxidation of acetaldehyde and the presence of a zirconium co-catalyst are also known to enhance the rate of conversion. However, when the cobalt-catalyzed oxidation of toluene is carried out in benzoic acid solvent in the absence of a halide promoter, the rate of the oxidation is too slow to be of practical use. The slow rate is observed even in the presence of a zirconium promoter.

Thus, there is a need for a catalyst system and method for oxidizing toluene to benzoic acid in benzoic acid solvent that is free of halide, especially one that has a high enough oxidation rate to be of practical use.

The present invention addresses this need as well as others, which will become apparent from the following description and the appended claims.

SUMMARY OF THE INVENTION

The invention is as set forth in the appended claims.

Briefly, in one aspect, the present invention provides a catalyst system for oxidizing toluene to benzoic acid in a solvent comprising benzoic acid. The catalyst system comprises:
  (a) a cobalt compound;
  (b) a zirconium compound or a hafnium compound or both; and
  (c) an alkali metal basic salt,
wherein the molar ratio of alkali metal to cobalt ranges from 0.1:1 to 1:1, and
wherein the catalyst system is free of a halogen compound as promoter.

In another aspect, the present invention provides a process for preparing benzoic acid from toluene. The process comprises:
  contacting toluene with an oxygen source in the presence of a catalyst system comprising (a) a cobalt compound, (b) a zirconium compound or a hafnium compound or both, and (c) an alkali metal basic salt in a solvent comprising benzoic acid at conditions effective to produce benzoic acid,
wherein the molar ratio of alkali metal to cobalt ranges from 0.1:1 to 1:1, and
wherein the contacting step is carried out in the absence of a halogen compound as promoter.

DETAILED DESCRIPTION OF THE INVENTION

It has been found, surprisingly, that the presence of a small amount of an alkali metal basic salt (for example, sodium benzoate) in the reactor results in a dramatic increase in the rate of oxidation of toluene to benzoic acid when the oxidation is carried out in a liquid medium composed primarily of benzoic acid.

Thus, in one aspect, the present invention provides a catalyst system for oxidizing toluene to benzoic acid in a solvent comprising benzoic acid. The catalyst system comprises:
  (a) a cobalt compound;
  (b) a zirconium compound or a hafnium compound or both; and
  (c) an alkali metal basic salt,
wherein the molar ratio of alkali metal to cobalt ranges from 0.1:1 to 1:1, and
wherein the catalyst system is free of a halogen compound as promoter.

The particular sources of cobalt, zirconium, and hafnium useful in the catalyst system of the invention are not particularly limiting, so long as the compounds are soluble or can be solubilized in the liquid reaction mixture under oxidization reaction conditions. Examples of suitable cobalt compounds include cobalt benzoate, cobalt (II) acetate tetrahydrate, cobalt (III) acetate, cobalt naphthenate, and cobalt acetylacetonate. Mixtures of cobalt compounds may be used. The concentration of cobalt (metal) in the reaction mixture can range from 500 ppm to 4,000 ppm, based on the total weight of the reaction mixture. Preferably, the cobalt concentration ranges from 2,000 to 3,500 ppm.

Examples of suitable zirconium compounds include zirconium benzoate, zirconium acetate, and zirconium acetylacetonate. Mixtures of zirconium compounds may also be used.

Examples of suitable hafnium compounds include hafnium benzoate, hafnium acetate, and hafnium acetylacetonate. Mixtures of hafnium compounds may also be used.

The amount of Zr and/or Hf used can vary over a wide range. For example, the molar ratio of zirconium and/or hafnium to cobalt (on an elemental basis) can range from 1:1 to 1:150.

The alkali metal basic salt in the catalyst system of the invention may be any salt of an alkali metal that hydrolyzes to form a basic solution, provided that the salt is soluble or can be solubilized in the reaction mixture under reaction conditions. Examples of alkali metals include lithium, sodium, potassium, rubidium, and cesium. Sodium is preferred. Examples of sodium basic salts include sodium oxide, sodium hydroxide, sodium peroxide, sodium carbonate, sodium bicarbonate, sodium acetate, and sodium benzoate. Similar salts of other alkali metals can also be used.

Preferably, the molar ratio of alkali metal to cobalt (on an elemental basis) in the reaction mixture ranges from 0.2:1 to 1:1, from 0.5:1 to 1:1, from 0.2:1 to 0.85:1, or from 0.5:1 to 0.85:1.

The catalyst system may be prepared by adding the components to a reaction solvent comprising benzoic acid, optionally with stirring and/or heating. In one embodiment, the catalyst components are dissolved in the solvent.

The reaction mixture in which the catalyst system is used is composed primarily of the benzoic acid solvent. For example, benzoic acid may be present in the reaction mixture in an amount of greater than 50 wt %, greater than 60 wt %, greater than 70 wt %, greater than 75 wt %, greater than 80 wt %, greater than 85 wt %, greater than 90 wt %, or greater than 95 wt %.

The reaction mixture/solvent may further comprise acetaldehyde and/or water. Co-oxidation of acetaldehyde can enhance the reaction rate afforded by the catalyst system of the invention. The amount of acetaldehyde used can range from 5% to 20% of the molar amount of toluene, with 8 to 12% being preferred. Preferably, acetic acid is not added to the reaction mixture or solvent. Alternatively, the reaction mixture or solvent is free of acetic acid.

Water in minor amounts may be added to the reaction mixture, for example, up to 10 wt %. In the case of a continuous process, the concentration of water in the reaction mixture is typically maintained between 3 to 10 wt %.

The catalyst system of the invention advantageously can provide a high rate of oxidation without using a halogen promoter. As such, the catalyst system of the invention can be free of a halogen compound as promoter.

By "free" or "in the absence of," it is meant that the recited component is not added to the catalyst system/reaction mixture or is not added in an amount that has a demonstrable effect on the production of benzoic acid or a deleterious effect on the process equipment.

The catalyst system according to the invention is particularly useful for oxidizing toluene to benzoic acid. Thus, in another aspect, the present invention provides a process for preparing benzoic acid from toluene. The process comprises contacting toluene with an oxygen source in the presence of the catalyst system described herein, in a solvent comprising benzoic acid at conditions effective to produce benzoic acid. The molar ratio of alkali metal to cobalt in the reaction mixture ranges from 0.1:1 to 1:1, and the contacting step is carried out in the absence of a halogen compound as promoter.

The process according to the invention may be performed batch-wise or continuously.

The oxidation reaction is carried out with the aid of a source of oxygen. The oxygen source is not particularly limiting. It is typically introduced in gaseous form. Examples of gases that can be used include air, oxygen-enriched air, air diluted with nitrogen, pure oxygen, ozone, and mixtures of these gases.

Typical oxidation conditions may be used in the process of the invention. The reaction temperature and pressure are not critical provided that a liquid phase is maintained in the reactor during the reaction. Generally, the reaction temperature can range from 135 to 180° C., with 160 to 170° C. being preferred. The reaction pressure can range from 2 atm (200 kPa) to 20 atm (2000 kPa), or from 3 atm (300 kPa) to 8 atm (800 kPa).

The process according to the invention can achieve a high rate of toluene conversion. Preferably, the toluene conversion rate is greater than 15%, greater than 20%, greater than 25%, greater than 30%, greater than 35%, greater than 40%, greater than 45%, greater than 50%, greater than 55%, or greater than 65%. In one preferred embodiment, the toluene conversion rate ranges from 40% to 70%.

Preferably, the process of the invention provides a benzoic acid yield of greater than 10%, greater than 20%, greater than 30%, greater than 40%, or greater than 50%.

Preferably, the process is carried out without adding a free radical initiator such as azobisisobutyronitrile (AIBN).

The benzoic acid produced may be recovered by techniques known in the art.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

EXAMPLES

Materials

Aqueous hydrobromic acid (48.7%) and sodium hydroxide were purchased from J.T. Baker. Cobalt (II) acetate tetrahydrate, manganese (II) acetate, 15 wt % zirconium acetate solution in acetic acid, 32 wt % peracetic acid solution in acetic acid, toluene, and acetaldehyde were purchased from Aldrich. 2-Ethoxybenzoic acid was received from Alfa-Aesar. All chemicals were used as received.

Analytical—Gas Chromatographic Method

Process samples were analyzed using a Shimadzu gas chromatograph Model 2010 (or equivalent) equipped with a split/heated injector (250° C.) and a flame ionization detector (250° C.). A capillary column (60 meter×0.32 mm ID) coated with 100% dimethylpolysiloxane (DB-1 or equivalent) at 1.0 μm film thickness was employed. Hydrogen was used as the carrier gas with an initial column head pressure of 13.3 psi and an initial column flow of 3.30 mL/minute, while the carrier gas linear velocity of 50.0 cm/second was maintained constant throughout the entire oven temperature program.

The column temperature was programmed as follows:

The initial oven temperature was set at 50° C. and was held for 4 minutes, the oven was ramped up to 250° C. at 20° C./minute and was held at 250° C. for 8 minutes (the total run time was 22.0 mins).

1.0-μL of the prepared sample solution was injected with a split ratio of 100:1. EZ-Chrom Elite chromatography data system software was used for data acquisition and data processing. The sample preparation was done by weighing 0.05 g (accurate to 0.1 mg) of sample in a GC vial and adding 200.0 μL of ISTD solution (1% by volume of decane in pyridine) and 1000 μL of BSTFA (N,O-bis(trimethylsilyl) trifluoroacetamide) with 1% TMSCI (trimethylchlorosilane) to the GC vial. The content was heated at 80° C. for 30 minutes to ensure complete derivatization. 1.0-μL of this prepared sample solution was injected for GC analysis.

Conversion and Yield

Conversion is defined as the moles of toluene reacted divided by moles of toluene fed.

Yield is defined as the moles of each reaction product species created per mole of toluene reacted. Yield calculations do not include unreacted toluene.

Example 1

Comparative

Benzoic acid (152.4 g, 1247.9 mmol), Co(OAc)$_2$4H$_2$O (1.9 g, 7.7 mmol), Mn(OAc)$_2$ (0.053 g, 0.31 mmol), 48.7 wt % aqueous hydrobromic acid (0.67 g, 4.0 mmol), and water (9.0 g, 499 mmol) were transferred to a 300-mL titanium autoclave equipped with a high pressure condenser, a baffle, and an Isco pump. The autoclave was pressurized with approximately 50 psig of nitrogen, and the mixture was heated to 165° C. in a closed system (i.e., with no gas flow) with stirring. At reaction temperature, an air flow of 1500 sccm was introduced at the bottom of the solution, and the reaction pressure was adjusted to 100 psig pressure. Toluene was fed to the mixture at a rate of 0.35 mL/min via a high pressure Isco pump (this is t=0 for the reaction time).

After 30 seconds from the start of toluene feeding, 1.0 g of 32 wt % peracetic acid in 5.0 mL of acetic acid was introduced using a blow-case to start the reaction. The feed was stopped after 1 hour, and the reaction continued for an additional hour at the same conditions of air flow, temperature, and pressure.

After the reaction time was completed, the air flow was stopped, and the autoclave was cooled to room temperature, depressurized, and unloaded. The solid product was analyzed by Gas Chromatography using BSTFA derivatization method. The off-gas was analyzed for CO and CO$_2$ by ND-1R (ABB, Advanced Optima) and O$_2$ by a paramagnetism detection system (Servomex, 1440 Model).

The results are given in Table 1.

Example 2

Comparative

Example 1 was repeated using the catalysts and hold time given in Table 1. The results are given in Table 1.

Example 3

Comparative

Example 1 was repeated using the catalysts and hold time given in Table 1. In this example, 2-ethoxybenzoic acid was used as the solvent in place of benzoic acid. The results are given in Table 1.

Examples 4 and 5

Comparative

Example 1 was repeated using the catalysts and reaction conditions given in Table 1. The results are given in Table 1.

TABLE 1

Catalyzed air oxidation of toluene in benzoic acid and 2-ethoxybenzoic acid solvents

| Ex. No. | Catalyst Comp. (ppm) | Rxn Time (hr) | P (psig) | T (° C.) | Conv. (%) | Yield Based on Recovered Mass (%) | | | |
|---|---|---|---|---|---|---|---|---|---|
| | | | | | | Benzaldehyde | Benzyl Alcohol | Benzyl Acetate | Benzyl Benzoate |
| 1 | Co (2464) Mn (91) Br (1760) | 2 | 100 | 165 | 99.7 | 0.2 | 0 | 0 | 0 |
| 2 | Co (3504) Zr (775) | 4 | 100 | 165 | <10 | 0.4 | 0 | 0 | 0.12 |
| 3 | Co (3503) Zr (775) | 4 | 100 | 135 | <10 | 0.3 | 0 | 0 | 0.2 |
| 4 | Co (107) | 4 | 150 | 185 | <10 | 0 | 0 | 0 | 0 |
| 5 | Co (70) Mn (298) | 4 | 150 | 185 | <10 | 0.3 | 0 | 0.1 | 0.2 |

Example 6

Comparative

Benzoic acid (150 g, 1228.3 mmol), Co(OAc)$_2$4H$_2$O (2.8 g, 11.2 mmol), 15.9 wt % Zr(OAc)$_4$ in acetic acid (0.92 g, 1.6 mmol), toluene (1.3 g, 14.1 mmol), and water (4.5 g, 249.7 mmol) were transferred to a 300-mL titanium autoclave equipped with a high pressure condenser, a baffle, and an Isco pump. The autoclave was pressurized with approximately 50 psig of nitrogen, and the mixture was heated to 165° C. in a closed system (i.e., with no gas flow) with stirring. At reaction temperature of 165° C., air (750 sccm) and nitrogen (750 sccm) flows were introduced at the bottom of the solution, and the reaction pressure was adjusted to 100 psig pressure.

A toluene-acetaldehyde mixture (68.5 wt % toluene and 31.5 wt % acetaldehyde) was fed at a rate of 0.18 mL/min via a high pressure Isco pump (this is t=0 for the reaction time). The feed was stopped after 3 hours, and the reaction continued for an additional hour at the same conditions of air flow, temperature and pressure. The total reaction time was 4 hours.

After the reaction time was completed, the air and nitrogen flows were stopped, and the autoclave was cooled to room temperature, depressurized and unloaded. The solid product was analyzed by Gas Chromatography using BSTFA derivatization method. The off-gas was analyzed for CO and $CO_2$ by ND-1R (ABB, Advanced Optima) and $O_2$ by a paramagnetism detection system (Servomex, 1440 Model).

The results are given in Table 2.

Example 7

Comparative

Benzoic acid (150 g, 1228.3 mmol), $Co(OAc)_2 4H_2O$ (2.8 g, 11.2 mmol), 15.9 wt % $Zr(OAc)_4$ in acetic acid (0.92 g, 1.6 mmol), toluene (1.3 g, 14.1 mmol), and water (4.5 g, 249.7 mmol) were transferred to a 300-mL titanium autoclave equipped with a high pressure condenser, a baffle, and two Isco pumps. The autoclave was pressurized with approximately 50 psig of nitrogen, and the mixture was heated to 165° C. in a closed system (i.e., with no gas flow) with stirring. At reaction temperature of 165° C., an air flow of 1500 sccm was introduced at the bottom of the solution, and the reaction pressure was adjusted to 100 psig pressure.

Toluene was fed to the mixture at a rate of 0.175 mL/min via a high pressure Isco pump one (this is t=0 for the reaction time). A toluene-acetaldehyde mixture (50.0 wt % toluene and 50.0 wt % acetaldehyde) was fed at a rate of 1.0 mL/min via a high pressure Isco pump 2 for 2.5 min to initiate the reaction. The feed from Isco pump one was stopped after 2 hours, and the reaction continued for an additional two hours at the same conditions of air flow, temperature, and pressure. The total reaction time was 4 hours.

After the reaction time was completed, the air and nitrogen flows were stopped, and the autoclave was cooled to room temperature, depressurized, and unloaded. The solid product was analyzed by Gas Chromatography using BSTFA derivatization method. The off-gas was analyzed for CO and $CO_2$ by ND-1R (ABB, Advanced Optima) and $O_2$ by a paramagnetism detection system (Servomex, 1440 Model).

The results are given in Table 2.

Example 8

Example 7 was repeated in presence of 532 ppm of Na (source: NaOH). A toluene-acetaldehyde mixture (50.0 wt % toluene and 50.0 wt % acetaldehyde) was fed at a rate of 1.0 mL/min via a high pressure Isco pump 2 for 2.5 min to initiate the reaction. The catalyst composition and results are given in Table 2.

As seen from Table 2, when Na was used as part of the catalyst, the toluene conversion increased from 38% (Example 7) to 62.7% (Example 8).

Example 9

Example 8 was repeated in presence of 1150 ppm of Na. A toluene-acetaldehyde mixture (50.0 wt % toluene and 50.0 wt % acetaldehyde) was fed at a rate of 1.0 mL/min via a high pressure Isco pump 2 for 2.5 min to initiate the reaction. The reaction time was 3 hours, and the pressure was 100 psig. The catalyst composition, reaction temperature, and results are given in Table 3.

Example 10

Example 8 was repeated in presence of 719 ppm of Na. A toluene-acetaldehyde mixture (50.0 wt % toluene and 50.0 wt % acetaldehyde) was fed at a rate of 1.54 mL/min via a high pressure Isco pump 2 for 2.5 min to initiate the reaction. The reaction time was 3 hours, and the pressure was 100 psig. The catalyst composition, reaction temperature, and results are given in Table 3.

Example 11

Example 8 was repeated in presence of 288 ppm of Na. A toluene-acetaldehyde mixture (50.0 wt % toluene and 50.0 wt % acetaldehyde) was fed at a rate of 1.0 mL/min via a high pressure Isco pump 2 for 2.5 min to initiate the reaction. The reaction time was 3 hours, and the pressure was 100 psig. The catalyst composition, reaction temperature, and results are given in Table 3.

Example 12

Example 8 was repeated in presence of 288 ppm of Na. A toluene-acetaldehyde mixture (50.0 wt % toluene and 50.0 wt % acetaldehyde) was fed at a rate of 2.1 mL/min via a high pressure Isco pump 2 for 2.5 min to initiate the reaction. The reaction time was 3 hours, and the pressure was 100 psig. The catalyst composition, reaction temperature, and results are given in Table 3.

Example 13

Example 8 was repeated in presence of 288 ppm of Na. A toluene-acetaldehyde mixture (50.0 wt % toluene and 50.0 wt % acetaldehyde) was fed at a rate of 1.0 mL/min via a high pressure Isco pump 2 for 2.5 min to initiate the reaction.

TABLE 2

Catalyzed air oxidation of toluene in benzoic acid in presence of acetaldehyde

| Ex. No. | Catalyst Comp. (ppm) | Mole Ratio of Toluene To Acetaldehyde | Conversion (%) | Yield Based on Recovered Mass (%) | | | |
|---|---|---|---|---|---|---|---|
| | | | | Benzaldehyde | Benzyl Alcohol | Benzyl Acetate | Benzyl Benzoate |
| 6 | Co (3508) Zr (776) | 1.1 | 66 | 3.1 | 0.2 | 0.1 | 0.2 |
| 7 | Co (3512) Zr (777) | 9.6 | 38 | 0.9 | 0 | 0 | 0.4 |
| 8 | Co (3509) Zr (776) Na (532) | 9.6 | 62.7 | 2.7 | 0 | 0 | 1.4 |

The reaction time was 3 hours, and the pressure was 100 psig. The catalyst composition, reaction temperature, and results are given in Table 3.

Example 14

Example 8 was repeated in presence of 719 ppm of Na. A toluene-acetaldehyde mixture (50.0 wt % toluene and 50.0 wt % acetaldehyde) was fed at a rate of 1.54 mL/min via a high pressure Isco pump 2 for 2.5 min to initiate the reaction. The reaction time was 3 hours, and the pressure was 100 psig. The catalyst composition, reaction temperature, and results are given in Table 3.

Example 15

Example 8 was repeated in presence of 288 ppm of Na. A toluene-acetaldehyde mixture (50.0 wt % toluene and 50.0 wt % acetaldehyde) was fed at a rate of 2.1 mL/min via a high pressure Isco pump 2 for 2.5 min to initiate the reaction. The reaction time was 3 hours, and the pressure was 100 psig. The catalyst composition, reaction temperature, and results are given in Table 3.

Example 16

Example 8 was repeated in presence of 1150 ppm of Na. A toluene-acetaldehyde mixture (50.0 wt % toluene and 50.0 wt % acetaldehyde) was fed at a rate of 2.1 mL/min via a high pressure Isco pump 2 for 2.5 min to initiate the reaction. The reaction time was 3 hours, and the pressure was 100 psig. The catalyst composition, reaction temperature, and results are given in Table 3.

Example 17

Example 8 was repeated in presence of 719 ppm of Na. A toluene-acetaldehyde mixture (50.0 wt % toluene and 50.0 wt % acetaldehyde) was fed at a rate of 1.54 mL/min via a high pressure Isco pump 2 for 2.5 min to initiate the reaction. The reaction time was 3 hours, and the pressure was 100 psig. The catalyst composition, reaction temperature, and results are given in Table 3.

Example 18

Example 8 was repeated in presence of 1150 ppm of Na. A toluene-acetaldehyde mixture (50.0 wt % toluene and 50.0 wt % acetaldehyde) was fed at a rate of 2.1 mL/min via a high pressure Isco pump 2 for 2.5 min to initiate the reaction. The reaction time was 3 hours, and the pressure was 100 psig. The catalyst composition, reaction temperature, and results are given in Table 3.

Example 19

Example 8 was repeated in presence of 1150 ppm of Na. A toluene-acetaldehyde mixture (50.0 wt % toluene and 50.0 wt % acetaldehyde) was fed at a rate of 1.0 mL/min via a high pressure Isco pump 2 for 2.5 min to initiate the reaction. The reaction time was 3 hours, and the pressure was 100 psig. The catalyst composition, reaction temperature, and results are given in Table 3.

TABLE 3

Catalyzed air oxidation of toluene in benzoic acid in presence of acetaldehyde and sodium ion

| Ex. No. | Catalyst Comp. (ppm) | MRTA | T (° C.) | Conv. (%) | Yield Based on Recovered Mass (%) | | | | |
|---|---|---|---|---|---|---|---|---|---|
| | | | | | BAH | BAL | BAC | BB | Phenol |
| 9 | Co (500) Zr (127) Na (1150) | 9.6 | 135 | 45.7 | 0.2 | 0.2 | 0 | 0.2 | 0.04 |
| 10 | Co (2000) Zr (508) Na (719) | 6.4 | 155 | 49.8 | 0.1 | 0.1 | 0 | 0.1 | 0.48 |
| 11 | Co (500) Zr (127) Na (288) | 9.6 | 175 | 49.4 | 0.2 | 0.2 | 0 | 0 | 1.16 |
| 12 | Co (3500) Zr (888) Na (288) | 4.8 | 175 | 58.2 | 0.3 | 0 | 0 | 0.3 | 0.17 |
| 13 | Co (3500) Zr (888) Na (288) | 9.6 | 135 | 41.8 | 0.4 | 0 | 0 | 0 | 0.1 |
| 14 | Co (2000) Zr (508) Na (719) | 6.4 | 155 | 44.3 | 0.2 | 0 | 0 | 0.3 | 0.03 |
| 15 | Co (500) Zr (127) Na (288) | 4.8 | 135 | 50.8 | 0.7 | 0 | 0 | 0.4 | 0.21 |
| 16 | Co (3500) Zr (888) Na (1150) | 4.8 | 135 | 65.9 | 0.5 | 0 | 0 | 0.2 | 0.08 |

TABLE 3-continued

Catalyzed air oxidation of toluene in benzoic acid in presence of acetaldehyde and sodium ion

| Ex. No. | Catalyst Comp. (ppm) | MRTA | T (° C.) | Conv. (%) | Yield Based on Recovered Mass (%) | | | | |
|---|---|---|---|---|---|---|---|---|---|
| | | | | | BAH | BAL | BAC | BB | Phenol |
| 17 | Co (2000) Zr (508) Na (719) | 6.4 | 155 | 46.8 | 0.5 | 0 | 0 | 0 | 0.02 |
| 18 | Co (500) Zr (127) Na (1150) | 4.8 | 175 | 54.0 | 0.3 | 0 | 0 | 0 | 0.10 |
| 19 | Co (3500) Zr (888) Na (1150) | 9.6 | 175 | 50.9 | 0.3 | 0 | 0 | 0 | 0.20 |

In Table 3, MRTA represents the mole ratio of toluene to acetaldehyde, BAH represents benzaldehyde, BAL represents benzyl alcohol, BAC represents benzyl acetate, and BB represents benzyl benzoate.

The invention has been described in detail with particular reference to preferred embodiments thereof, but it will be understood that variations and modifications can be effected within the spirit and scope of the invention.

We claim:

1. A process for preparing benzoic acid from toluene, comprising:
   contacting toluene with an oxygen source in the presence of a catalyst system comprising (a) a cobalt compound, (b) a zirconium compound or a hafnium compound or both, and (c) an alkali metal basic salt in a solvent mixture comprising benzoic acid, wherein said benzoic acid is present in an amount greater than 50 weight percent of the total weight of the catalyst system and solvent mixture, at conditions effective to produce benzoic acid,
   wherein the molar ratio of alkali metal to cobalt ranges from 0.1:1 to 1:1, and
   wherein the contacting step is carried out in the absence of a halogen compound as promoter.

2. The process according to claim 1, wherein the cobalt compound is selected from the group consisting of cobalt benzoate, cobalt (II) acetate tetrahydrate, cobalt (III) acetate, cobalt naphthenate, or mixtures thereof.

3. The process according to claim 1, wherein the zirconium compound is selected from the group consisting of zirconium benzoate, zirconium acetate, zirconium acetylacetonate, or mixtures thereof.

4. The process according to claim 1, wherein the hafnium compound is selected from the group consisting of hafnium benzoate, hafnium acetate, hafnium acetylacetonate, or mixtures thereof.

5. The process according to claim 1, wherein the alkali metal basic salt is selected from the group consisting of lithium, sodium, potassium, rubidium, or cesium.

6. The process according to claim 1, wherein the alkali metal basic salt is sodium.

7. The process according to claim 6, wherein the alkali metal basic salt is selected from the group consisting of sodium oxide, sodium hydroxide, sodium peroxide, sodium carbonate, sodium bicarbonate, sodium acetate, and sodium benzoate.

8. The process according to claim 1, wherein the molar ratio of alkali metal to cobalt ranges from 0.2:1 to 0.85:1.

9. The process according to claim 1, wherein the molar ratio of zirconium to cobalt ranges from 1:1 to 1:150.

10. The process according to claim 1, wherein the solvent is free of acetic acid.

11. The process according to claim 1, wherein the solvent mixture further comprises acetaldehyde.

12. The process according to claim 1, wherein cobalt is present in an amount ranging from 500 to 4,000 ppm, based on the total weight of the solvent mixture and catalyst system.

13. The process according to claim 1, wherein cobalt is present in an amount ranging from 2,000 to 3,500 ppm, based on the total weight of the solvent mixture and catalyst system.

* * * * *